United States Patent
Sholev et al.

(10) Patent No.: US 10,456,202 B2
(45) Date of Patent: *Oct. 29, 2019

(54) DEVICE AND METHODS OF IMPROVING LAPAROSCOPIC SURGERY

(71) Applicant: TransEnterix Europe S.a.r.l., Lugano (TI) (CH)

(72) Inventors: Mordehai Sholev, Amikam (IL); Gal Atarot, Kfar Saba (IL); Motti Frimer, Zichron Yaakov (IL)

(73) Assignee: TransEnterix Europe S.a.r.l., Lugano (TI) (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/817,223

(22) Filed: Aug. 4, 2015

(65) Prior Publication Data
US 2016/0184031 A1 Jun. 30, 2016
US 2017/0119480 A9 May 4, 2017

Related U.S. Application Data

(63) Continuation-in-part of application No. 11/874,534, filed on Oct. 18, 2007, now Pat. No. 9,295,379, which
(Continued)

(51) Int. Cl.
*A61B 34/10* (2016.01)
*A61B 1/00* (2006.01)
(Continued)

(52) U.S. Cl.
CPC .......... *A61B 34/10* (2016.02); *A61B 1/00006* (2013.01); *A61B 1/00016* (2013.01);
(Continued)

(58) Field of Classification Search
CPC ............ A61B 1/00016; A61B 1/00039; A61B 1/00149; A61B 19/22; A61B 2019/2207;
(Continued)

(56) References Cited

U.S. PATENT DOCUMENTS 5,836,869 A * 11/1998 Kudo ................. A61B 1/00039
600/102
5,867,308 A * 2/1999 Pensel ................. A61B 3/0025
359/368

(Continued)

*Primary Examiner* — Anh Tuan T Nguyen
*Assistant Examiner* — William B Chou

(57) ABSTRACT

A device to direct an endoscope to follow a surgical instrument during laparoscopic surgery, comprising an automated assistant mechanically interconnected to the endoscope, and at least one wireless transmitter with at least one operating key, where the wireless transmitter is in communication with a wireless receiver. The wireless receiver is in communication with the wireless receiver and with the automated assistant. The automated assistant can load surgical instrument spatial locating software and automated assistant maneuvering software and can provide a visual onscreen depiction of the field of view, including any surgical instruments therein. Depression of an operating key selects an instrument, which is then automatically followed by the endoscope. The operating key can be attached to an instrument or can be freestanding.

22 Claims, 5 Drawing Sheets

Related U.S. Application Data is a continuation of application No. PCT/IL2006/000478, filed on Apr. 20, 2006, application No. 14/817,223, filed on Aug. 4, 2015, which is a continuation of application No. 13/736,118, filed on Jan. 8, 2013, now Pat. No. 9,943,372, which is a continuation-in-part of application No. 11/874,534, filed on Oct. 18, 2007, now Pat. No. 9,295,379, and a continuation of application No. PCT/IL2013/000312, filed on Aug. 21, 2012.

(60) Provisional application No. 60/705,199, filed on Aug. 4, 2005, provisional application No. 60/716,953, filed on Sep. 15, 2005, provisional application No. 60/716,951, filed on Sep. 15, 2005, provisional application No. 60/672,010, filed on Apr. 18, 2005, provisional application No. 61/525,785, filed on Aug. 21, 2011.

(51) Int. Cl.

| | | |
|---|---|---|
| *A61B 1/313* | (2006.01) | |
| *A61B 34/00* | (2016.01) | |
| *A61B 34/30* | (2016.01) | |
| *A61B 34/20* | (2016.01) | |
| *G08C 17/02* | (2006.01) | |
| *A61B 17/00* | (2006.01) | |
| *A61B 90/10* | (2016.01) | |
| *A61B 90/00* | (2016.01) | |
| *A61B 90/53* | (2016.01) | |

(52) U.S. Cl.
CPC ...... *A61B 1/00039* (2013.01); *A61B 1/00045* (2013.01); *A61B 1/00149* (2013.01); *A61B 1/3132* (2013.01); *A61B 17/00234* (2013.01); *A61B 34/25* (2016.02); *A61B 34/30* (2016.02); *A61B 34/70* (2016.02); *A61B 34/74* (2016.02); *A61B 90/10* (2016.02); *A61B 90/361* (2016.02); *A61B 90/53* (2016.02); *G08C 17/02* (2013.01); *A61B 2017/00221* (2013.01); *A61B 2034/2057* (2016.02); *A61B 2034/301* (2016.02); *A61B 2034/302* (2016.02); *A61B 2090/3612* (2016.02); *A61B 2090/373* (2016.02); *G08C 2201/30* (2013.01); *G08C 2201/92* (2013.01)

(58) Field of Classification Search
CPC .... A61B 2019/2211; A61B 2019/2215; A61B 34/20; A61B 34/25; A61B 34/32; A61B 34/35; A61B 34/37; A61B 2034/2068; A61B 2090/371
USPC ........ 600/102, 103, 109, 114, 117, 118, 160, 600/173, 424, 429; 606/1, 130
See application file for complete search history.

(56) References Cited

U.S. PATENT DOCUMENTS

| | | | |
|---|---|---|---|
| 5,876,325 A * | 3/1999 | Mizuno | A61B 1/00048 600/102 |
| 6,714,841 B1 | 3/2004 | Wright et al. | |
| 2003/0055409 A1 * | 3/2003 | Brock | A61B 5/04 606/1 |
| 2004/0044295 A1 * | 3/2004 | Reinert | A61B 17/1757 600/587 |
| 2004/0243147 A1 * | 12/2004 | Lipow | G09B 23/28 606/130 |
| 2006/0152516 A1 * | 7/2006 | Plummer | G06F 19/321 345/538 |
| 2006/0264742 A1 * | 11/2006 | Neubauer | A61B 90/36 600/424 |
| 2018/0325604 A1 * | 11/2018 | Atarot | A61B 5/7425 |

* cited by examiner

DEVICE AND METHODS OF IMPROVING LAPAROSCOPIC SURGERY

FIELD OF THE INVENTION

The present invention generally relates to means and methods for improving the interface between the surgeon and the operating medical assistant or between the surgeon and an endoscope system for laparoscopic surgery. Moreover, this present invention discloses a device useful for controlling an endoscope system for laparoscopic surgery, in which the endoscope is inserted through a small incision into the body's cavities.

BACKGROUND OF THE INVENTION

In laparoscopic surgery, the surgeon performs the operation through small holes using long instruments and observing the internal anatomy with an endoscope camera. The endoscope is conventionally held by a camera human assistant (i.e. operating medical assistant) since the surgeon must perform the operation using both hands. The surgeon performance is largely dependent on the camera position relative to the instruments and on a stable image shown at the monitor. The main problem is the difficulty for the operating medical assistant to hold the endoscope steadily, keeping the scene upright.

Laparoscopic surgery is becoming increasingly popular with patients because the scars are smaller and their period of recovery is shorter. Laparoscopic surgery requires special training of the surgeon or gynecologist and the theatre nursing staff. The equipment is often expensive and not available in all hospitals.

During laparoscopic surgery it is often required to shift the spatial placement of the endoscope in order to present the surgeon with the optimal view. Conventional laparoscopic surgery makes use of either human assistants that manually shift the instrumentation or alternatively robotic automated assistants. Automated assistants utilize interfaces that enable the surgeon to direct the mechanical movement of the assistant, achieving a shift in the camera view.

U.S. Pat. No. 6,714,841 discloses an automated camera endoscope in which the surgeon is fitted with a head mounted light source that transmits the head movements to a sensor, forming an interface that converts the movements to directions for the mechanical movement of the automated assistant. Alternative automated assistants incorporate a voice operated interface, a directional key interface, or other navigational interfaces. The above interfaces share the following drawbacks:
  a. Single directional interface that provide limited feedback to the surgeon
  b. Cumbersome serial operation for starting and stopping movement directions that requires the surgeon's constant attention, preventing the surgeon from keeping the flow of surgical procedure.

Research has suggested that these systems divert the surgeons focus from the major task at hand. Therefore technologies assisted by magnets and image processing have been developed to simplify interfacing control. However these improved technologies still fail to address another complicating interface aspect of laparoscopic surgery, they do not allow the surgeon to signal to both the automated assistant and to human assistants or to surgical colleagues, which instrument his attention is focused on.

Hence, there is still a long felt need for a improving the interface between the surgeon and an endoscope system, surgical colleagues or human assistants for laparoscopic surgery.

SUMMARY OF THE INVENTION

It is one object of the present invention to disclose a device useful for the surgeon and the automated assistant interface, and/or said surgeon and the operating medical assistant interface, during laparoscopic surgery; wherein said device is adapted to control and/or direct said automated endoscope assistant to focus said endoscope on the desired instrument of said surgeon; further wherein said device is adapted to focus said operating medical assistant on said desired instrument of said surgeon.

It is another object of the present invention to disclose the device as defined above, wherein said device additionally comprising:
  a. at least one wireless transmitter with at least one operating key;
  b. at least one wireless receiver;
  c. at least one conventional laparoscopy computerized system; said conventional laparoscopy computerized system is adapted to load a surgical instrument spatial locating software, and an automated assistant maneuvering software; said locating software enables a visual response to the depression of said at least one key on said wireless transmitter; said maneuvering software enables the movement of said endoscope; and
  d. at least one video screen.

It is another object of the present invention to disclose the device as defined above, wherein each said instrument is fitted with a wireless transmitter.

It is another object of the present invention to disclose the device as defined above, wherein said wireless transmitter is freestanding.

It is another object of the present invention to disclose the device as defined above, wherein said wireless transmitter is adapted to locate the position of each instrument.

It is another object of the present invention to disclose the device as defined above, wherein said selection of said desired instrument is confirmed by clicking on said at least one key.

It is another object of the present invention to disclose the device as defined above, wherein said selection of said desired instrument is confirmed by depression of said at least one key on said wireless transmitter.

It is another object of the present invention to disclose the device as defined above, wherein said depression of said at least one key is a prolonged depression.

It is another object of the present invention to disclose a method useful for surgeon and the automated assistant interface, and/or said surgeon and the operating medical assistant interface, during laparoscopic surgery. The method comprises step selected inter alia from (a) obtaining a device as defined above; (b) selecting said desired instrument; and (c) displaying said desired instrument on a screen; wherein said device controlling and/or directing said automated endoscope assistant and thereby focusing said endoscope on said desired instrument of said surgeon.

It is another object of the present invention to disclose the method as defined above, additionally comprising the step of confirming by the selection of said desired instrument.

It is another object of the present invention to disclose the method as defined above, additionally comprising the step of extracting said desired instrument form said screen.

It is another object of the present invention to disclose the method as defined above, additionally comprising the step of instructing said automated assistant to focus said endoscope on said desired instrument.

It is another object of the present invention to disclose the method as defined above, wherein said step of selecting said desired instrument additionally comprising the steps of (a) depressing of said at least one key on said wireless transmitter; (b) transmitting a generic code to said receiver; (c) communicating said signal to the computer.

It is another object of the present invention to disclose the method as defined above, wherein said step of selecting said desired instrument additionally comprising the step confirming the selection of said desired instrument by clicking on said at least one key.

It is another object of the present invention to disclose the method as defined above, wherein said step of selecting said desired instrument additionally comprising the step confirming the selection of said desired instrument by a prolonged depression on said at least one key.

It is another object of the present invention to disclose the method as defined above, additionally comprising the step of re-selecting said desired instrument until said desired instrument is selected.

It is another object of the present invention to disclose the method as defined above, additionally comprising the step of identifying each of said instruments to said computerized system.

It is another object of the present invention to disclose the method as defined above, additionally comprising the step of attaching said wireless transmitter to said surgical instrument.

It is another object of the present invention to disclose the method as defined above, additionally comprising the step of matching each transmitted code from said depressed wireless transmitter to said surgical instrument.

It is another object of the present invention to disclose the method as defined above, wherein said step of matching each transmitted code additionally comprising the step of storing said matching database on a computer.

It is another object of the present invention to disclose the method as defined above, additionally comprising the step of signing said surgical instrument by a temporary onscreen graphic symbol and presenting upon the onscreen depiction of the surgical instrument.

It is another object of the present invention to disclose the method as defined above, additionally comprising the step of continuously displaying said selection graphic symbol.

It is still an object of the present invention to disclose the method as defined above, wherein the selection of the surgical instrument is signified by a continuous onscreen graphic symbol presented upon the onscreen depiction of the surgical instrument.

It is lastly an object of the present invention to disclose the method as defined above, additionally comprising the step of calculating the position of each said instrument.

BRIEF DESCRIPTION OF THE FIGURES

In order to understand the invention and to see how it may be implemented in practice, and by way of non-limiting example only, with reference to the accompanying drawing, in which.

DETAILED DESCRIPTION OF THE EMBODIMENTS

Figure 1:
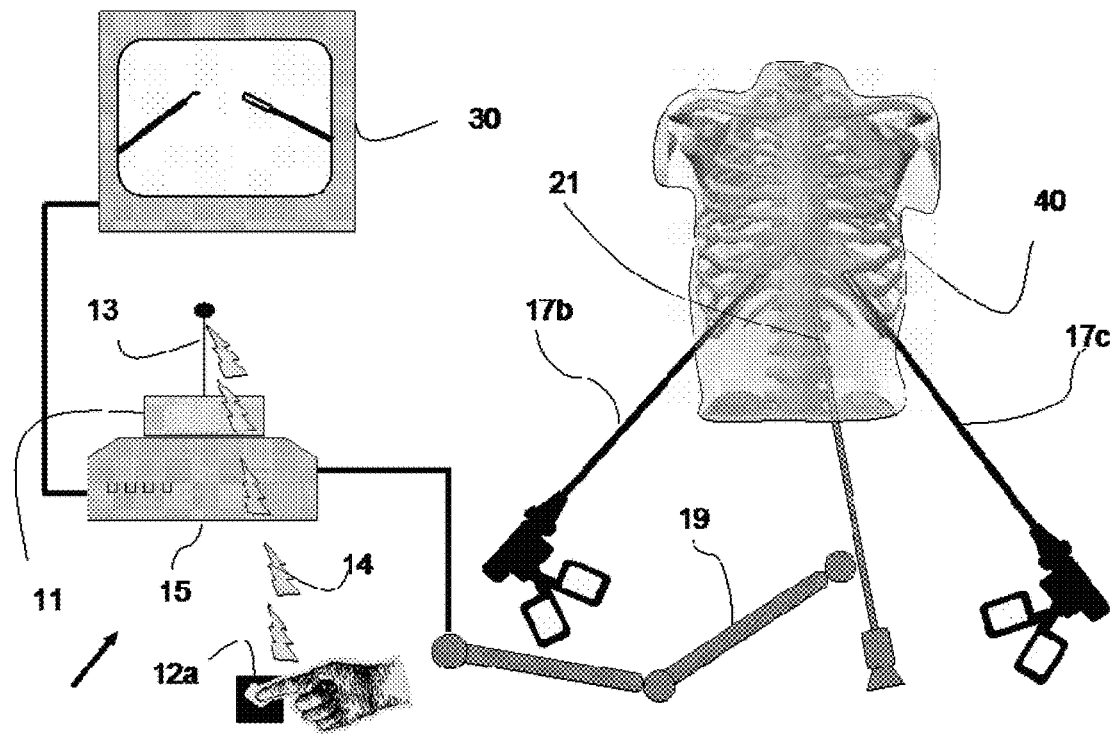
FIG. 1 is a general schematic view of an enhanced interface laparoscopic system that relies on a single wireless code signal to indicate the instrument on which to focus the endoscope constructed in accordance with the principles of the present invention in a preferred embodiment thereof.

The following description is provided, alongside all chapters of the present invention, so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide means and methods for improving the interface between the surgeon and an endoscope system for laparoscopic surgery.

The present invention can be also utilized to improve the interface between the surgeon and the operating medical assistant and/or the surgeon colleagues. Moreover, the present invention can be also utilized to control and/or direct an automated endoscope assistant to focus the endoscope to the desired instrument of the surgeon. Furthermore, the device is adapted to focus the operating medical assistant on the desired instrument of the surgeon.

The term "conventional laparoscopy computerized system" refers herein to system or/software conventionally used in the market such as Lapman, Endo assist or AESOP.

In preferred embodiment of the invention a single wireless emission code is utilized and choice is achieved by a visible graphic representation upon the conventional viewing screen.

In another preferred embodiment each instrument is fitted with a unique code wireless transmitter, and selection is achieved by depressing its button.

The present invention discloses also a device joined with conventional camera assisted laparoscopic surgery systems comprising at least one wireless transmitter that may or may not be attached to the maneuvering control end of surgical instruments. Upon depression of at least one button on the transmitters either a generic or a unique code is transmitted to a receiving device connected to a computer that presents (e.g. displays) the selected surgical tool on a connected video screen. Confirmation of the selection by the depression of at least one button on wireless transmitter transmits a code to the receiver connected to the computer that instructs the automated surgical assistant to move the endoscope achieving a view on the screen that is focused on the selected instrument area.

It would thus be desirable to achieve a device that allows the surgeon to identify to the laparoscopic computing system as well as to surgical colleagues to which surgical instrument attention is to be directed. By identifying the surgical instrument by the laparoscopic computing system the endoscope directs the view to the selected focus of attention.

Therefore, in accordance with a preferred embodiment of the present invention an enhanced interface laparoscopy device is provided. The device comprising:

a. At least one wireless transmitter with at least one operating key.
b. At least one wireless receiver.
c. at least one conventional laparoscopy computerized system; said conventional laparoscopy computerized system is adapted to load a surgical instrument spatial locating software, and an automated assistant maneuvering software; said locating software enables a visual response to the depression of said at least one key on said wireless transmitter; said maneuvering software enables the movement of said endoscope.
d. At least one video screen.
e. At least one automated assistant.

In a preferred embodiment of the enhanced interface laparoscopy device the wireless transmitter or transmitters are either freestanding or attached to the maneuvering end of the surgical instruments and emit the same single code that upon the depression of at least one key on them emits a signal to the receiver that communicates with the connected computer that displays a graphic symbol upon a random choice of one of the onscreen surgical instruments depicted or extracted by the computer on the screen. If needed the surgeon repeats the depression of at least one key resulting in a shift in the displayed graphic designator from one onscreen depiction of surgical instrument to another until the desired instrument is reached and thereby selected. Subsequently the computer directs the automated assistant to focus the endoscope on the desired instrument area.

In a further preferred embodiment the selection of the instrument requires confirmation by varying the form of click on at least one key, such as a prolonged depression. Only upon confirmation is the computer authorized to instruct the automated assistant to focus the endoscope on the desired instrument area.

In another preferred embodiment of the invention each relevant surgical instruments is fitted at its maneuvering control end with a wireless transmitter with at least one key that transmits a unique code. In the initial stage of the procedure the surgeon identifies each of the instruments to the computerized system by depressing at least one key on each of the wireless transmitters fitted to the surgical instruments and matching their characteristics with a prepared database, thereby forming within the computerized system a unique signature for each of the transmitters. Thereon, upon depression of at least one key on the wireless transmitter attached to each surgical instrument, the receiver receives the unique code communicates it to the computer that identifies it with the preprogrammed signature and instructs the automated assistant to move the endoscope so as to achieve the desired focus.

In another preferred embodiment of the invention each relevant surgical instruments is fitted at its maneuvering control end with a wireless transmitter with at least one key that transmits a unique code. While performing the surgery procedure, whenever the surgeon inserts, a surgical instrument at the first time, he signals by depressing at least one key on each of the wireless transmitters fitted to the surgical instruments.

Then the computer software identifies the instrument, while it is being inserted, analyzes the characteristics of the surgical instrument and keeps it in a database, thereby forming within the computerized system a unique signature for each of the transmitters. Thereon, upon depression of at least one key on the wireless transmitter attached to each surgical instrument, the receiver receives the unique code, communicates it to the computer that identifies it with the signature stored at the insertion step and instructs the automated assistant to move the endoscope so as to achieve the desired focus.

In a further preferred embodiment the selection is signified on the connected screen by displaying a graphic symbol upon the onscreen depiction of the surgical.

In a further preferred embodiment the selection is confirmed by an additional mode of depression of at least one key on the wireless transmitter, such as a prolonged depression of the key, authorizing the computer to instruct the automated assistant to change view provided by the endoscope.

The device of the present invention has many technological advantages, among them:

Simplifying the communication interface between surgeon and mechanical assistants.
Seamless interaction with conventional computerized automated endoscope systems.
Simplicity of construction and reliability.
User-friendliness
Additional features and advantages of the invention will become apparent from the following drawings and description.

Reference is made now to FIG. 1, which is a general schematic view of an enhanced interface laparoscopic system comprising one or more button operated wireless transmitters 12a, that may or may not be attached to the maneuvering end of surgical instruments 17b and 17c, which once depressed aerially transmit a single code wave 14 through aerial 13 to connected receiver 11 that produces a signal processed by computer 15 thereby assigning a particular one of two or more surgical instruments 17b and 17c as the focus of the surgeons attention. Accordingly a conventional automated endoscope 21 is maneuvered by means of conventional automated arm 19 according to conventional computational spatial placement software contained in computer 15.

Figure 2:
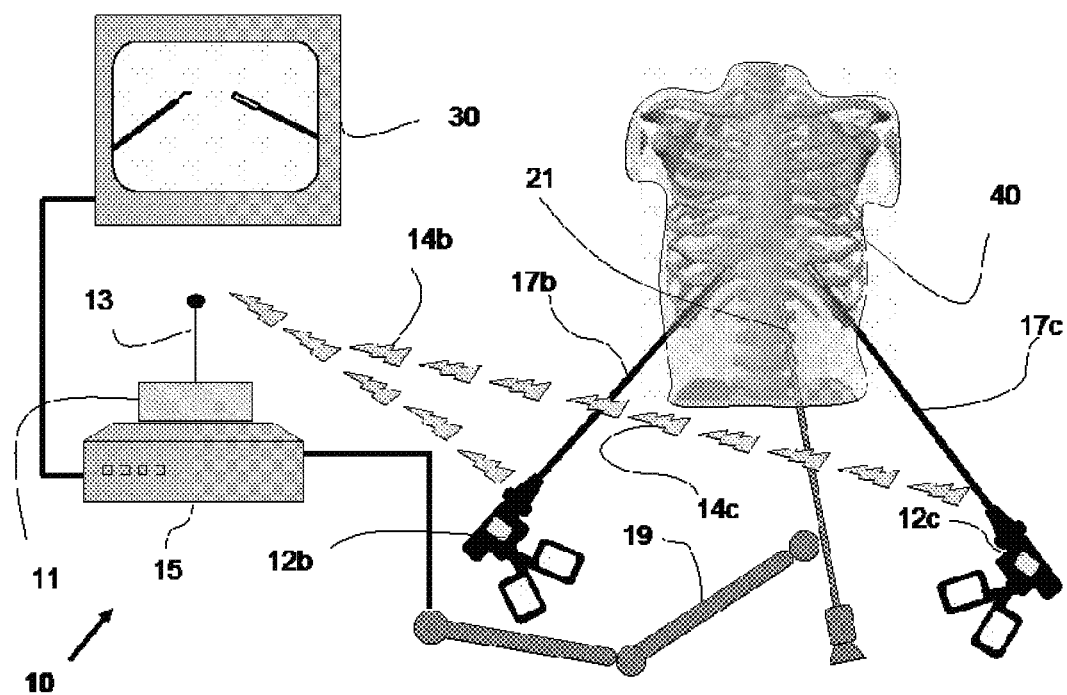
FIG. 2 is a general schematic view of an enhanced interface laparoscopic system that relies on at least two wireless signals to indicate the instrument on which to focus the endoscope.

Reference is made now to FIG. 2, which is a general schematic view of an enhanced interface laparoscopic system comprising one or more button operated wireless transmitters 12b and 12c are attached respectfully to the maneuvering means at the end of surgical instruments 17b and 17c, which once depressed aerially, each transmit a unique code wave 14b and 14c through aerial 13 to connected receiver 11 that produces a signal processed by computer 15 thereby assigning a particular one of two or more surgical instruments 17b and 17c as the focus of the surgeons attention. Accordingly a conventional automated endoscope 21 is maneuvered by means of conventional automated arm 19 according to conventional computational spatial placement software contained in computer 15.

Figure 3:
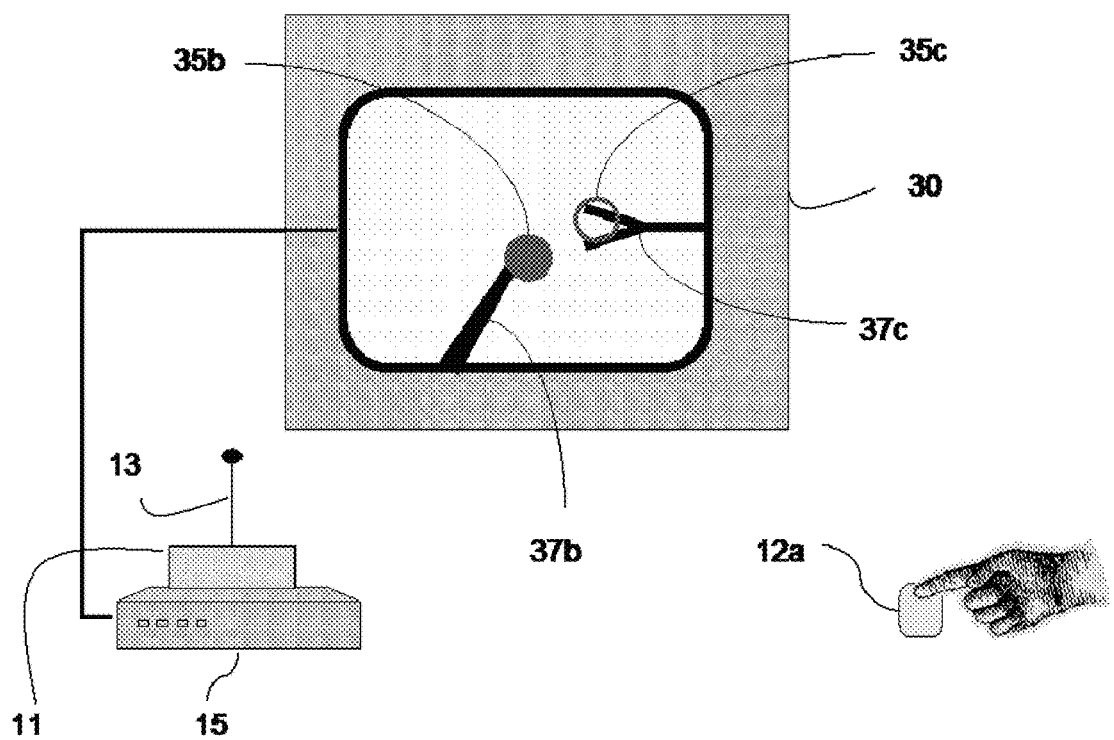
FIG. 3 is a schematic view of the method in which the single wireless code signal choice instrumentation focus is represented on the viewing apparatus.

Reference is made now to FIG. 3, which is a schematic view of the method in which single wireless signal code choice of instrumentation focus is achieved, by means of video representation, 35b and 35c of the actual surgical instruments (not represented in FIG. 3) displayed by graphic symbols. Wherein a light depression of the button on generic code emitting wireless transmitter 12a transmits a code that is received by receiver aerial 13 communicated through connected receiver 11 to computer 15 that shifts the graphically displayed symbol of choice 35b on video screen 30 from instrument to instrument until the required instrument is reached. A prolonged depression of the button on transmitter 12a confirms the selection thereby signaling computer 15 to instruct the automated mechanical assistant (not represented in FIG. 4) to move the endoscope (not represented in FIG. 3) and achieving a camera view of the instrument area on screen 30.

Figure 4:
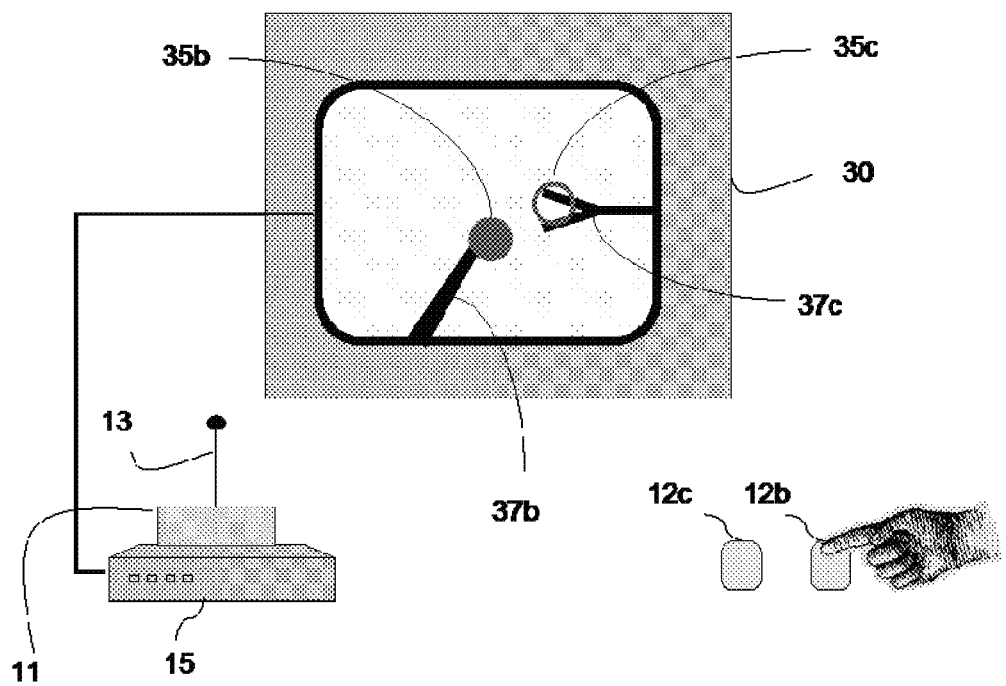
FIG. 4 is a schematic view of the method in which multiple wireless code signal choice of instrumentation is operated.

Reference is made now to FIG. 4, which is a schematic view of the method in which multiple wireless signal code choice of instrumentation focus is achieved, by means of video representation 35b and 35c of the actual surgical instruments (not represented in FIG. 4) displayed by graphic symbols. Wherein when buttons on unique code emitting wireless transmitters 12b and 12c attached respectfully to actual operational instruments (not represented in FIG. 4) displays graphic symbol 35b on respectful video representation 37b. A prolonged depression of the button on transmitter 12b and 12c confirms the selection thereby signaling computer 15 to instruct the automated mechanical assistant (not represented in FIG. 4) to move the endoscope (not represented in FIG. 4) and achieving a camera view of the instrument area on screen 30.

In another embodiment of this invention, when a prolonged depression of the buttons on transmitter 12b and 12c confirms the selection, the computer software analyze the characteristics of the surgical instrument and stores it in a database, thereby forming within the computerized system, a database, used for matching between each transmitting code and a surgical instrument.

From now on, when the surgeon presses again on this button, the receiver that receives the transmitted code, communicates it to the computer software that identifies the code as a "known" code and matching it, to the known parameters that were stored earlier in database of the surgical tools, and extracts the surgical tool tip. When the position tool tip is known, then the tracking software instructs the automated assistant to move the endoscope so as to achieve the desired focus.

Figure 5:
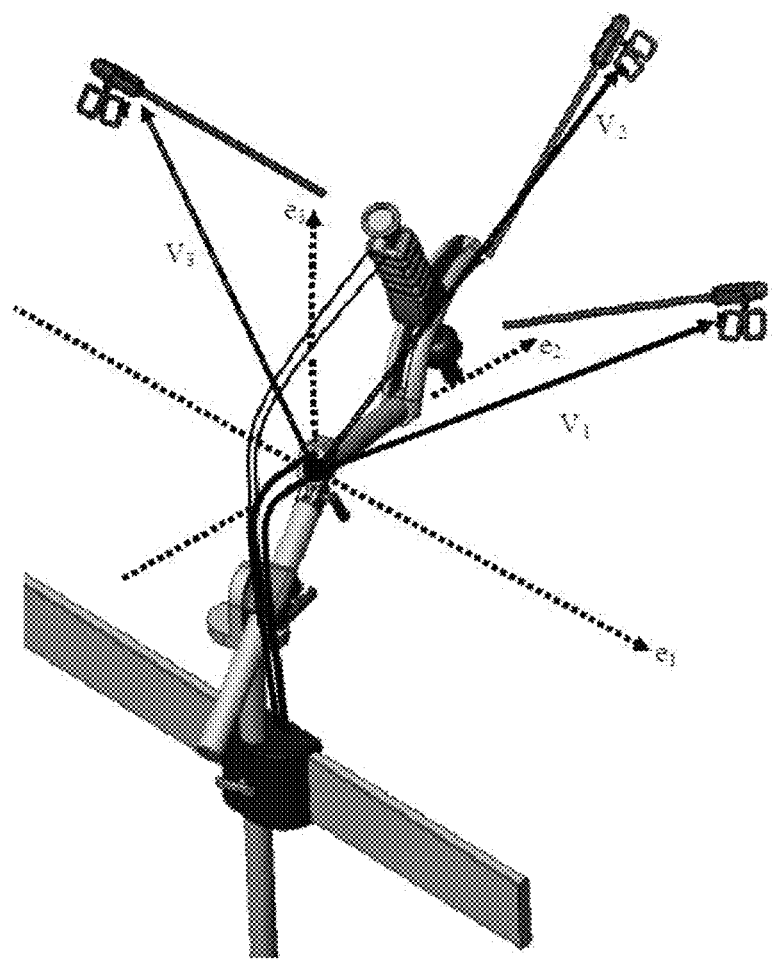
FIG. 5 represents the relative position of each tool in respect to the mechanism.

Reference is made now to FIG. 5 illustrating the relative position of each tool. While performing the surgery, the surgeon often changes the position of his tools and even their insertion point. The wireless switches then may be use to locate the relative angle in which each tool is being held in respect to the camera holder mechanism. This is another advantage of the system that is used to calculate the position of the tool in the frame captured by the video camera. In that manner the surgeon does not have to inform the system where the insertion point of every tool is. The exact location of the wireless switch is not measured: the information about the relative positions of the tools in respect to each other contains in most cases enough data for the software to maintain the matching between the switches and the tools. In this figure the positioning sensors of the system are placed near or on the camera holder so the signals they receive can be utilize in order to calculate the vectors V1 V2 . . . Vn representing the range and the 3 angles needed to define a point in a 3D space.

In order to realize a position and range system, many well known technologies may be used. For example if the switches emit wireless signals then an array of antennas may be used to compare the power of the signal received at each antenna in order to determine the angle of the switch and it's approximate range to the camera holder mechanism. If the switch emits ultra sound wave then US microphones can be used to triangulate the position of the switch. The same is for light emitting switch.

The invention claimed is:

1. A device useful for a surgeon and an automated assistant interface, and/or said surgeon and an operating medical assistant interface, during laparoscopic surgery; wherein said device comprises:
   a. an endoscope, mechanically interconnectable to an automated assistant;
   b. at least one instrument;
   c. at least one wireless transmitter with at least one operating key; said wireless transmitter and said at least one operating key are in communication with at least one of said at least one instrument; said wireless transmitter is configured to transmit a signal once said at least one operating key is pressed;
   d. at least one wireless receiver; configured to receive said signal sent by said transmitter; and
   e. at least one conventional laparoscopy computerized system in communication with said wireless receiver and said automated assistant;
   wherein said signal sent is associated with said at least one instrument such that once said at least one operating key is pressed said at least one instrument is selected;
   wherein said device is configured to control and to direct said endoscope via said conventional laparoscopy computerized system and said automated assistant on said at least one selected instrument;
   wherein said at least one selected instrument is selectable following a pressure on said at least one operating key;
   further wherein, upon said selection, electronic on-screen identification of a selected at least one laparoscopic instrument is providable, said electronic on-screen identification being real-time overlaid of a real-time image of said selected at least one laparoscopic instrument.

2. The device according to claim 1, wherein each said instrument is fittable with a wireless transmitter.

3. The device according to claim 2, wherein said wireless transmitter is configured to locate the position of each instrument.

4. The device according to claim 2, wherein said selection of said desired instrument is confirmed by clicking on said at least one operating key.

5. The device according to claim 2, wherein said selection of said desired instrument is confirmed by depression of said at least one operating key on said wireless transmitter.

6. The device according to claim 1, wherein said depression of said at least one operating key is a prolonged depression.

7. The system of claim 1, wherein said conventional laparoscopy computerized system is configured to execute surgical instrument spatial locating software and automated assistant maneuvering software; said conventional laparoscopy computerized system is configured to provide a visual onscreen depiction of at least one selected instrument.

8. The system of claim 1, additionally comprising at least one video screen.

9. A surgical system comprising:
   (a) at least one laparoscopic instrument;
   (b) at least one wireless transmitter configured to be activated to transmit a signal, said wireless transmitter in communication with said at least one laparoscopic instrument;
   (c) a computerized platform configured to receive said signal and to provide electronic visual identification of at least one selected laparoscopic instrument; and
   (d) an automated assistant in communication with said computerized platform configured to control a position of an endoscopic camera,
   wherein said signal sent is associated with said at least one laparoscopic instrument such that once at least one operating key is pressed said at least one laparoscopic instrument is selected;

wherein said at least one selected laparoscopic instrument is selectable by manual activation of said transmitter;

wherein said computerized platform is configured to (a) track said laparoscopic instrument selected using image information received from said endoscopic camera; and, (b) instruct the automated assistant to move said endoscopic camera to follow the movement of said laparoscopic instrument selected;

further wherein said electronic visual identification is displayable upon depression of said at lease one operating key, said electronic visual identification being real-time overlaid on a real-time image of said selected at least one laparoscopic instrument.

10. The system of claim 9, wherein said computerized platform is configured to track said at least one selected laparoscopic instrument.

11. The system of claim 9, wherein said at least one wireless transmitter is attachable to said at least one laparoscopic instrument.

12. The system of claim 9, wherein said at least one wireless transmitter is freestanding.

13. The system of claim 9, wherein said identifying of said laparoscopic instrument is effectible via a visual depiction of said laparoscopic instrument on a display.

14. The system of claim 13, wherein said computerized platform is configured to visually identify said laparoscopic instrument upon manual activation of said transmitter.

15. The system of claim 9, wherein said computerized platform is configured to control said automated assistant.

16. A surgical system comprising:
(a) at least one laparoscopic instrument;
(b) at least one wireless transmitter configured to be activated to transmit a signal, said wireless transmitter in communication with said at least one laparoscopic instrument;
(c) a computerized platform configured to receive said signal and to identify at least one selected laparoscopic instrument; and
(d) an automated assistant in communication with said computerized platform for controlling the position of an endoscopic camera;

wherein said signal sent is associated with said at least one laparoscopic instrument such that once at least one operating key is pressed said at least one laparoscopic instrument is selected;

wherein said selected laparoscopic instrument is selectable by manual activation of said transmitter;

wherein said computerized platform is configured to (a) track said laparoscopic instrument selected using image information received from said endoscopic camera; and, (b) instruct the automated assistant to move said endoscopic camera according to movement of said laparoscopic instrument selected;

further wherein, upon said selection, on-screen electronic visual identification of a selected at least one laparoscopic instrument is providable, said on-screen electronic visual identification being real-time overlaid on a real-time image of said selected at least one laparoscopic instrument.

17. The system of claim 16, wherein said computerized platform is configured to track said at least one selected laparoscopic instrument.

18. The system of claim 16, wherein said at least one wireless transmitter is attachable to said at least one laparoscopic instrument.

19. The system of claim 16, wherein said at least one wireless transmitter is freestanding.

20. The system of claim 16, wherein said identifying of said laparoscopic instrument is effected via a visual depiction of said laparoscopic instrument on a display.

21. The system of claim 16, wherein said computerized platform is configured to control said automated assistant.

22. The system of claim 16, wherein said computerized platform is configured to generate, upon manual activation of said transmitter, an electronic visual identifier for said laparoscopic instrument.

* * * * *